(12) United States Patent
Chen et al.

(10) Patent No.: US 9,737,255 B2
(45) Date of Patent: Aug. 22, 2017

(54) MEASURING COGNITIVE LOAD

(75) Inventors: Fang Chen, Peakhurst Heights (AU); Muhammad Asif Khawaja, Bankstown (AU); Eric Choi, West Pennant Hills (AU)

(73) Assignee: NATIONAL ICT AUSTRALIA LIMITED, Eveleigh, New South Wales (AU)

(*) Notice: Subject to any disclaimer, the term of this patent is extended or adjusted under 35 U.S.C. 154(b) by 2 days.

(21) Appl. No.: 13/120,902

(22) PCT Filed: Sep. 29, 2009

(86) PCT No.: PCT/AU2009/001289
§ 371 (c)(1),
(2), (4) Date: May 9, 2011

(87) PCT Pub. No.: WO2010/037163
PCT Pub. Date: Apr. 8, 2010

(65) Prior Publication Data
US 2011/0207099 A1    Aug. 25, 2011

(30) Foreign Application Priority Data
Sep. 30, 2008   (AU) .................................. 2008905089

(51) Int. Cl.
A61B 5/16      (2006.01)
A61B 5/00      (2006.01)
G10L 15/18     (2013.01)

(52) U.S. Cl.
CPC ............. *A61B 5/16* (2013.01); *A61B 5/4803* (2013.01); *A61B 5/7264* (2013.01);
(Continued)

(58) Field of Classification Search
CPC .............. A61B 5/16; A61B 5/165; G09B 7/00
(Continued)

(56) References Cited

U.S. PATENT DOCUMENTS 5,944,530 A *  8/1999  Ho et al. ........................ 434/236
6,061,610 A    5/2000  Boer
(Continued)

FOREIGN PATENT DOCUMENTS

EP    1 417 390     5/2004
JP    2004-233691   8/2004
(Continued)

OTHER PUBLICATIONS

W. Macdonald et al., "Effects of Workload level and 8- Versus 12-h Workday Duration on Test Battery Performance", International Journal of Industrial Ergonomics, 2000—26 (3), pp. 399-416.
(Continued)

*Primary Examiner* — Peter Egloff

(57) ABSTRACT

This invention concerns measuring cognitive load. A word based input is produced by a person while performing a task (100). Predetermined grammatical features of the word based input are identified (104). Then, the identified grammatical features are weighted and combined to provide a measure indicating the person's cognitive load (106). The use of grammatical features represents a divergence from the known methods of providing a measure of a person's cognitive load. It is an advantage of the invention that by concentrating on the grammatical features it is able to provide an objective, non-intrusive measure of the person's cognitive load. Aspects the invention include a method, a computer system and software that are used to perform the method.

13 Claims, 5 Drawing Sheets

(52) U.S. Cl.
CPC .......... *A61B 5/7475* (2013.01); *A61B 5/7267* (2013.01); *G10L 15/1815* (2013.01)

(58) Field of Classification Search
USPC ........................................ 434/227, 236, 323
See application file for complete search history.

(56) References Cited

U.S. PATENT DOCUMENTS

| | | | |
|---|---|---|---|
| 6,363,346 | B1 | 3/2002 | Walters |
| 6,390,979 | B1 | 5/2002 | Njemanze |
| 7,058,566 | B2 * | 6/2006 | Shaw ............................... 704/9 |
| 7,346,492 | B2 | 3/2008 | Shaw |
| 2002/0106617 | A1 * | 8/2002 | Hersh .......................... 434/236 |
| 2002/0116196 | A1 * | 8/2002 | Tran ...................... G06F 1/3203 704/270 |
| 2003/0050740 | A1 * | 3/2003 | Fecher et al. ..................... 701/1 |
| 2003/0212546 | A1 | 11/2003 | Shaw |
| 2004/0037236 | A1 | 2/2004 | Massey et al. |
| 2009/0298482 | A1 * | 12/2009 | Yen et al. .................. 455/414.2 |

FOREIGN PATENT DOCUMENTS

| | | |
|---|---|---|
| WO | WO 99/60546 | 11/1999 |
| WO | WO 2005/050522 | 6/2005 |
| WO | WO 2007/000030 | 1/2007 |

OTHER PUBLICATIONS

J. Tesak, "Cognitive Load and the Processing of Grammatical Items", Journal of Neurolinguistics, 1994, 8(1), pp. 43-48.

M. Fayol et al., "Cognitive Overload and Orthographic Errors: When Cognitive Overload Enhances Subject-Verb Agreement Errors. A Study in French Written Language", The Quarterly Journal of Experimental Psychology, 1994, 47A(2), pp. 437-464.

Grammar, Wikipedia, the free encyclopedia; http://en.wikipedia.org/siki/Grammar, Sep. 3, 2011, 6 pages.

P. Nickel et al., "Psychometric Properties of the 0.1 Hz component of HRV as an Indicator of Mental Strain", Proceedings of the IEA 2000/HFES 2000 Congress, 2000, 5 pages.

E. Bates et al., "On the Inseparability of Grammar and the Lexicon: Evidence from Acquisition, Aphasia and Real-Time Processing", Language and Cognitive Processes, 1997, 12(5/6), pp. 507-584.

M. Workman et al., "An Exploratory Study of Cognitive Load in Diagnosing Patient Conditions", International Journal of Quality in Health Care, 2007, 19(3), pp. 127-133.

S. Campbell, "$3^{rd}$ Party Remote Call Monitoring Feature: Speech Analytics Fastest Growing Application in Contact Center", TMCnet.com, Sep. 3, 2011, 3 pages.

F. Paas et al., "Cognitive Load Measurement as a Means to Advance Cognitive Load Theory", Educational Psychologist, 38(1), 2003, pp. 63-71.

Woldnet, A lexical database for English, Cognitive Science Laboratory, Princeton University, New Jersey http://worldnet.princeton.edu, Sep. 3, 2011, 3 pages.

Language Glossary, Dept. of Language and Logistics, University of Essex, Wivenhoe, Park, Colchester, United Kingdom, http://ww.esses.ac.uk/linguistics , Sep. 3, 2011, 2 pages.

PCT International Search Report and Written Opinion of the International Searching Authority, Application No. PCT/AU2009/001289, Australian Patent Office, Nov. 2009, 12 pages.

* cited by examiner

| Features / Data Sets | WordCount | Words/Sentence | LongWords | AffectiveWords | NegativeEmotions | Cognitive | Inclusive | Perception | Feelings |
|---|---|---|---|---|---|---|---|---|---|
| Level 2,3 | I | I, 0.005 | I | D, 0.08 | I, 0.002 | I | I, 0.06 | I | I, 0.006 |
| Level 1,4 | I | I | I | D | I | I, 0.04 | I, 0.02 | I, 0.048 | I, 0.04 |
| Role-wise 1,4 (IC) | I | I | I | D | I | I, 0.049 | I, 0.045 | I | I |
| Role-wise 1,3 (IC) | I, 0.006 | I, 0.06 | I | D | I, 0.08 | I | I, 0.047 | I, 0.04 | I, 0.09 |
| Role-wise 1,3 (Plan) | I, 0.07 | I | I, 0.08 | D, 0.045 | I, 0.006 | I | I, 0.02 | I, 0.04 | I, 0.01 |
| Role-wise 1,4 (Ops) | I | I | I | D | I | I | I | I | I |
| Role-wise 2,3 (IC) | I | I, 0.04 | I | D | I, 0.04 | I | I, 0.06 | I, 0.07 | I, 0.02 |
| Role-wise 2,3 (Plan) | I | I | I | D | I, 0.06 | I | I | I | I |
| Role-wise 2,3 (Ops) | I | I, 0.04 | I | D | I | I | I, 0.07 | I | I, 0.08 |

Fig. 5

MEASURING COGNITIVE LOAD

TECHNICAL FIELD

This invention concerns a method for measuring cognitive load. In other aspects the invention can be expressed as a computer system and as software that are used to perform the method.

The concept of cognitive load has been used in a variety of fields that deal with the human mind interacting with some external stimulants. The definition of cognitive load is slightly different in each field. For instance, in pedagogical literature cognitive load refers to the total amount of mental activity imposed on working memory at any instance in time; while in ergonomics literature it is described as the portion of operator information processing capacity, or resources that are required to meet cognitive task demands. Each field provides different methods to measure cognitive load.

In this specification the phrase "cognitive load" is defined as in the cognitive psychology literature, and its meaning is not a measurement of attention span, work load, stress, engagement or other external elements to a task. Cognitive load is defined here as the mental effort or demand required for a particular user to comprehend or learn some material, or complete some task [1]. Cognitive load is relative to both the user (i.e. their ability to process novel information) and the task being completed (i.e. complexity), at any single point in time. It is attributable to the limited capacity of a person's working memory and their ability to process novel information.

BACKGROUND ART

Conventional methods for measuring cognitive load, include:
- subjective measures, such as self-rating scales;
- physiological techniques, such as pupil dilatation, heart rate and galvanic skin responses;
- task or performance based measures, such as critical error rates and task completion times; and
- behavioural measures, such as speech disfluencies, self-talk etc.

There are a number of problems with these methods for measuring cognitive load, including:
- some of the methods are intrusive and disrupt the normal flow of performing the task;
- some of the methods are physically uncomfortable for the user;
- cannot be conducted in real-time as they are too labour-intensive;
- the data quality is potentially unreliable outside laboratory conditions; and
- the data quality can be affected by outside factors, such as user's stress level.

Objectively quantifying cognitive load that can be applied uniformly across fields as a standard, or to allow comparison between subjects remains an open problem. In fact, historically, the most consistent results for cognitive load assessments have been achieved through self-rating subjective measures. These allow users to describe in fine detail their perceived level of cognitive load induced by various types of task.

SUMMARY OF THE INVENTION

In a first aspect the invention provides a method for measuring a person's cognitive load, the method comprising the steps of:

(a) receiving, from an input device, words based input produced by a person while performing a task;
(b) identifying automatically, using a processor, predetermined grammatical syntactical, morphological and semantic features of the word based input; and
(c) weighting and combining the identified grammatical features in real-time or substantially real-time to provide a measure indicating the person's cognitive load.

Grammar is the branch of linguistics that deals with syntax (the use of words in the construction of phrases and sentences), morphology (internal structure of words), and also with semantics (meaning and inspiration) [2], [3]. Grammar covers the rules governing the use of any given natural language.

The invention concerns the discovery that grammatical features can be used to assess a person's cognitive load, and how they can be assessed by identification, weighting and combination. The use of grammatical features represents a divergence from the known methods of providing a measure of a person's cognitive load. It is an advantage of the invention that by concentrating on the grammatical features it is able to provide an objective measure of the person's cognitive load. It is a further advantage that it provides this measure in a non-intrusive manner. Since the invention only requires word based input, it can be applied to any task where the input is word based.

The method may also comprise the step of classifying the task, such as task type and task complexity. In this case, the predetermined grammatical features of step (b) may be weighted and combined in step (c) according to the task classification for more accurate cognitive load measurement.

The predetermined grammatical features of step (b) may include one or more of:
- identification of the number and types of parts of speech e.g. nouns, pronouns, propositions, verbs
- identification of number and types of grammatical errors made
- identification of the number and types of particular words and/or phrases at specific sentence and/or paragraph positions
- identification of the number of shorter or longer (i.e. six letters) words and/or sentences
- identification of semantics, meanings and interpretation of the words and/or sentences The word based input may be produced from speech of the person when performing the task. The speech may be automatically converted to text to form the word based input.

The method may further comprise classifying the task based on predetermined task and user profiles. These predetermined task and user profiles may be generated based on a training cycle. The training cycle may comprise identifying the grammatical features that are indicators of the person's cognitive load, and may be based on the specific task.

Steps (b) and (c) may be performed in substantially real time.

The word based input of step (a) may be text input that is typed by the person when performing the task. Alternatively, it may be written words that are automatically converted to electronic text.

The weighting and/or combining of step (c) may be based on the task, such as task domain or classification. The weighting may also be person dependent.

The method may further comprise the step of receiving physiological input about the person while performing the task. The method may further comprise in step (b) identifying predetermined physiological features from the physiological input that are indicative of the person's cognitive load. Alternatively, the weighting of step (c) may be influenced by the physiological input.

The method may further comprise the step of receiving environmental data about the environment of the person while performing the task. In that case, the weighting of step (c) may be influenced by the environmental data.

In a further aspect, the invention provides a computer system to measure a person's cognitive load while performing a task comprising:
- a receiver to receive, from an input device, word based input produced by a person while performing the task; and
- a classifier to identify predetermined syntactical, morphological and semantic features of the word based input; and
- a combiner to weight and combine the identified features in real-time or substantially real-time to provide a measure indicating the person's cognitive load.

In yet a further aspect, the invention provides software operable when installed on a computer that can interface with a person to perform the method of measuring the person's cognitive load as described above.

BRIEF DESCRIPTION OF THE DRAWINGS

An example of the invention will now be described with reference to the accompanying drawings, in which:

FIG. 5 is a table showing sample results of this example.

BEST MODES OF THE INVENTION

In complex, data-intense situations, users can experience high levels of cognitive load. This can interfere with their ability to complete a task and also adversely affect their performance of the task.

The intelligent user interface system of this example, which is aware of the user's changes in cognitive load can alleviate this problem by implementing output strategies to modulate the pace, content, and format of the output interaction in real-time and/or by determining the resources needed by the user to complete the task effectively and efficiently. The interface is aware of the user's cognitive load based on an assessment of the grammatical features of the user's speech input. This is to be contrasted with acoustic and phonetic features of the user's speech input.

Figure 1:
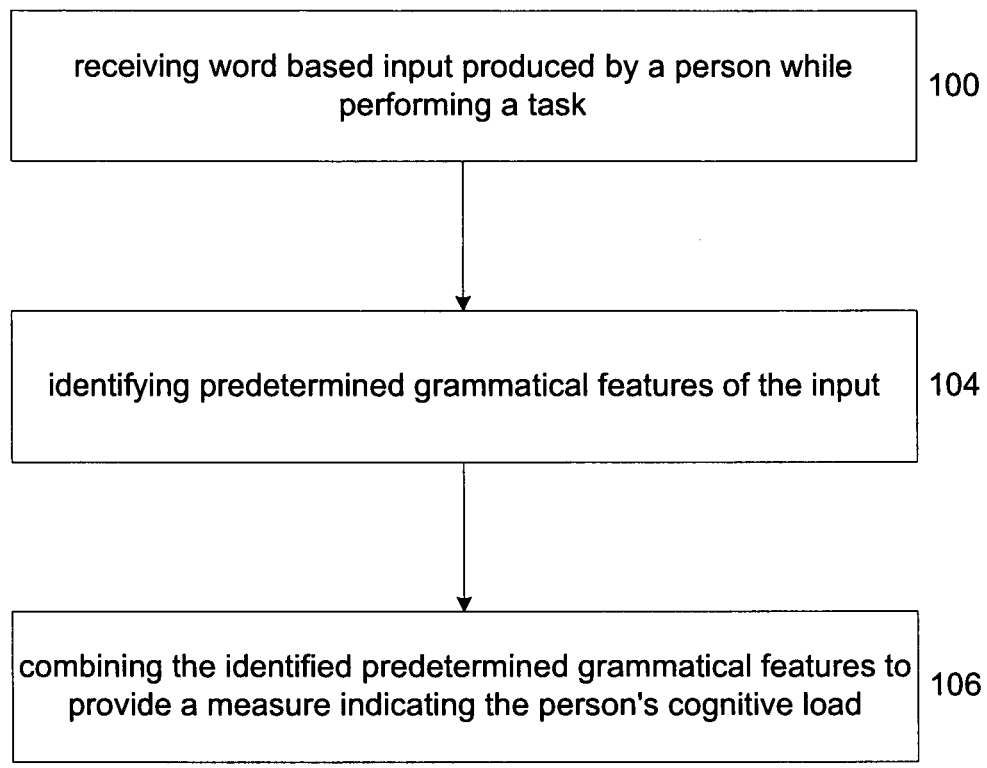
FIG. 1 is flow chart of this example of the current invention.

The method of measuring the user's cognitive load from which these output strategies will be based will now be described with reference to FIGS. 1 and 2. This example relates to on-line distance education. The learning cognitive load is a measure of the mental processing demand involved in learning tasks. When this demand is too high or low, learning is ineffective. The development of a voice analysis-based learning difficulty diagnosis program, which measures learning cognitive load, would contribute immediately to the improvement of education for rural and dispersed learners, who participate in tele-teaching, audio-conferencing, video-conferencing or who call help services, such as a help desk.

The determined cognitive load is provided in real time to the teacher, tutor or help desk operator to provide clearer information about students' learning difficulties than currently available diagnostic methods. The measurements of cognitive load can also be used to diagnose learning difficulties in conventional educational settings, and to assist in the development of instructional programs. Implementations of this invention could help provide both teachers and students immediate feedback about their learning effectiveness.

In this example the user 200, which is a student, is performing a task that is domain dependent, the domain in this case being on-line distance learning.

In performing the learning task, the user 200 interacts with the human-computer interface by providing speech. In alternative examples, the interface can be part of a computer assisted human-human interaction system such as the systems typically deployed in air traffic control, emergency services and call centres.

The components of the example interface of this example include:

The interaction system 202 which is comprised of system elements used to assist in the task. For example the hardware may be a computer having a display means such as a monitor that displays an interface. The interface can display a video conference screen of the teacher during a tutorial or questions that form a test. A receiver is also provided to receive word based input produced by a person while performing the task. For example, input means such as a keyboard to type answers to the question and a mouse to navigate the interface. A microphone is also provided to record the speech 212 of the user 200 as they perform the task, such as answering questions posed by the tutor on the video link or questions of the test. Further inputs are provided to, provide data on environmental factors 204, such as a thermometer, and physiological data 206, such as a heart rate monitor to provide heart rate data as input. The computer also includes a processor to guide the computer to perform the required interaction in accordance with instructions provided by software installed on the computer. The software is stored on a machine-readable medium which includes any mechanism that provides (i.e. stores and/or transmits) information in a form readable by a machine (e.g. a computer). For example, a machine-readable medium includes read only memory (ROM), random access memory (RAM), magnetic disk storage media, optical storage media, flash memory devices, and electrical, optical, acoustical or other forms of propagated signals (e.g. carrier waves, infrared signals, digital signals).

A user 200 completes the task, their speech is recorded and converted to text using a speech-to-text (STT) conversion component 214 in the form of software installed on the computer.

Task profiles/databases 208 stored in memory of the computer containing task characteristics, such as task type, task complexity or difficulty, current stage or state of the task, completion rate etc.

User profiles/databases 210 stored in the memory of the computer containing user characteristics such as gender, age, and education;

A cognitive load measurement component 216 receives the STT 214 output, classifies the task category or domain based on task 208 and user profiles 210, identifies and weights individual grammatical features for the classified task and combines them together with the appropriate combination function to achieve a cognitive load measure 218.

In this example, during training, the user 200 is required to complete a set of tasks using the speech-enabled interactive interface 202. They are able to use mainly their speech to interact with the system 202. As they complete the tasks, their speech, which includes their unconsciously-generated grammatical features, is recorded and fed 100 into a cognitive load analysis unit 216.

More specifically, the user 200 is assigned a set of tasks for the user to complete while interacting with the system 202. These tasks must have definite variation in complexity so that the measurements at each cognitive load level can be taken separately. Different methods of feature classification will be derived but not all may be applied depending on the task application instance.

As the user 200 completes the tasks, their speech is recorded 212 and converted to text transcriptions using a speech-to-text conversion component 214. This is non-intrusive, objective, and can be performed in real-time.

The cognitive load analysis component 216 receives the transcriptions (including time alignment information) and identifies/extracts any applicable set of selected grammatical feature categories 104 for each level of cognitive load. The feature categories that are chosen depend on the classified task application area. Therefore, only a few task specific features will be extracted by the cognitive load analysis unit.

Users 200 exhibit several grammatical changes in their natural language usage while interacting with the system that can be used to determine their cognitive load. A selection of grammatical features can be used for particular application domain and at particular time intervals for measuring cognitive load of a user. They are highly unobtrusive as the data can be collected while the subject completes some other tasks without them being aware of the cognitive load analysis taking place in real-time.

The grammatical features can be extracted from the spoken language, or the language that is typed directed into the system by the classifier. The grammatical features include:

Number and particular nouns, pronouns, anaphora, propositions, conjunctions, verbs (past tense, third person, singular verbs)
Use of a particular type of syntax or grammatical structure (i.e. usage of parts of speech and their forms)
Grammatical errors
Use of small or large number of particular words
Use of particular words and/or phrases at specific sentence and/or paragraph positions
Use of more shorter or longer (i.e. six letters) words and/or sentences
Number of words per sentence
Use of particular types of grammatical categories
Use of a particular meaning or interpretation of words and/or sentences These features are then calculated and weighted 106 for that user 200 and combined 106 together by the combiner using a feature combination method to acquire a reliable measure of the cognitive load.

Figure 3:
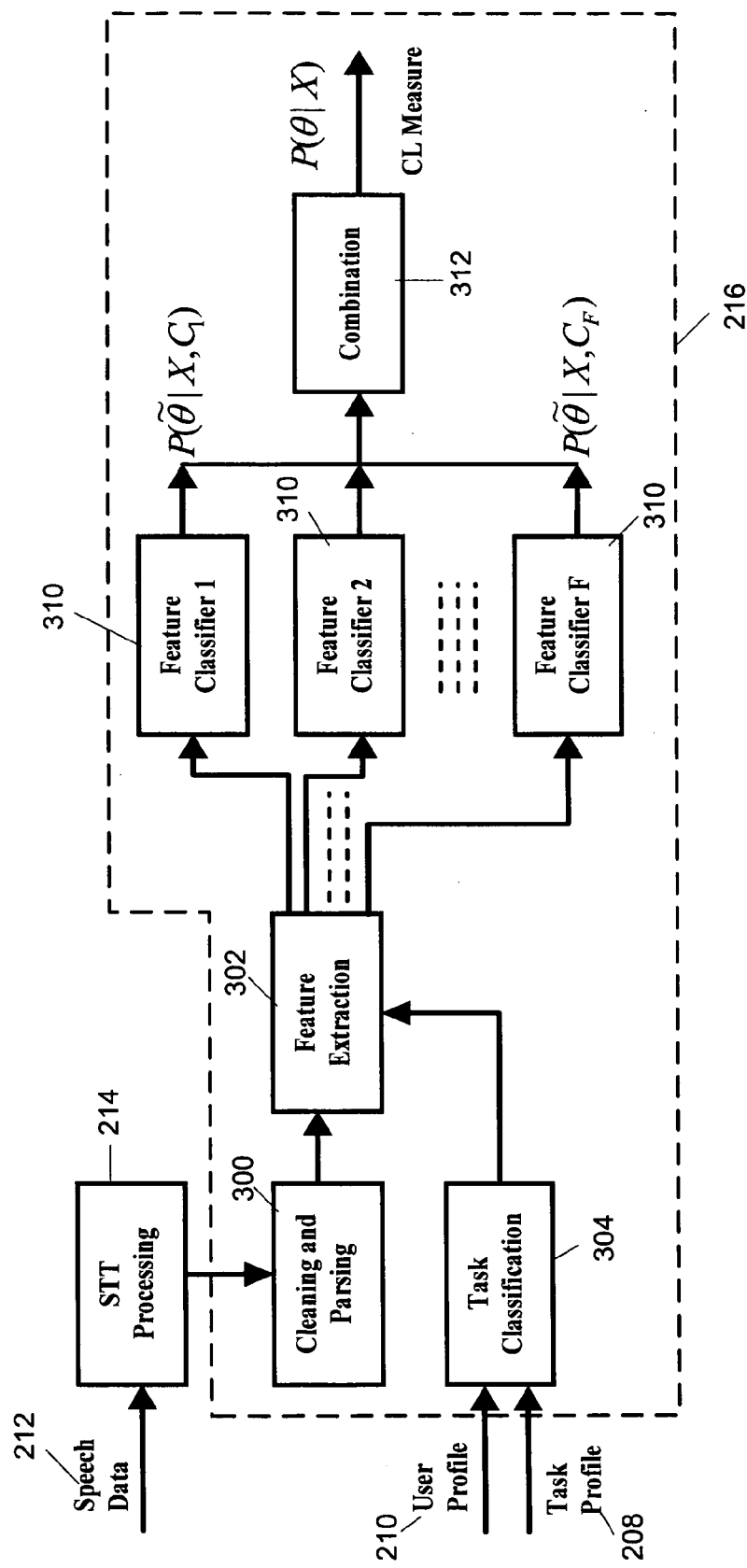
FIG. 3 is a schematic representation of this example of the current invention.

Referring now to FIG. 3 the method performed by the cognitive load analysis component 216 will now be described. The module 216 receives 100 the speech transcription generated by the STT conversion component 214. The module 216 then cleans the data and parses 300 it for feature extraction 302 requirements.

In control measurement mode (i.e. training), the module extracts 302 and records the relevant set of grammatical features from the parsed transcription at each level of cognitive load along with the user profile 210 and task 208 characteristics. All available user and task attributes are divided into homogeneous clusters based on clustering algorithm, such as Decision Tree. Each cluster can then be assigned a task ID where corresponding grammatical features can be tagged accordingly. Features from the higher load tasks can be assigned higher weights and given a larger significance during the actual measurement process later.

Figure 4:
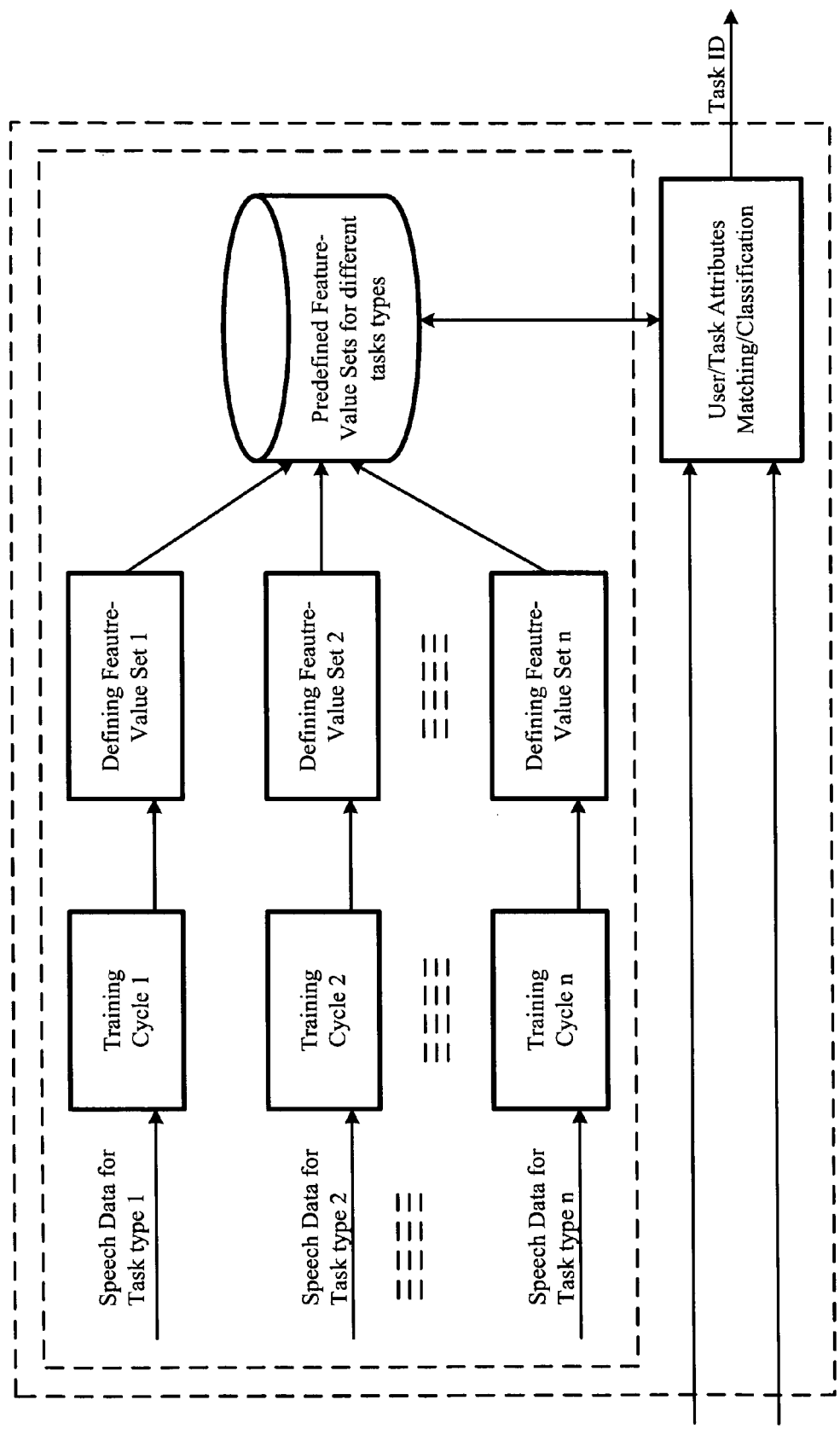
FIG. 4 is a schematic diagram of the task classification of the current invention.

In actual measurement mode (i.e. real-time assessment of cognitive load) the task is classified in 304, where a fast search is done to retrieve the task ID, for example, for an online learning or examination task with its difficulty level, subject type etc., from the Decision Tree built during training as shown in FIG. 4. The module 304 can also cover other application/task categories such as call centre operator training, bushfire management, traffic incident management, air traffic control, reading comprehension and collaborative problem solving. Based on this classification, the module 216 identifies 104 the grammatical features that are predetermined as relevant to that classification of task. For example, when the task is classified as an emergency management task, the predetermined features extracted from the parsed transcription can include:

Number of Words used,
Words per Sentence,
Words with at least six letters,
Frequency of Affective Words,
Frequency of Negative Emotion Words, and
Frequency of Cognitive Words that represent human cognitive processes.

Emphasis will be given to the Negative Emotions and Cognitive Words in this case. On the other hand when the task is classified as a reading task, the predetermined features to be extracted can include:

Frequency of Negative Emotion Words, and
Frequency of Cognitive Words.

Similarly, when the task is classified as a collaborative problem solving task, the predetermined features to be extracted from the transcription can include:

Pronouns Usage Pattern (both singular and plural pronouns),
Frequency of Agreements/Disagreements, and
Language Complexity.

The module 216 then extracts 302 these features from the parsed 300 transcription and calculates and assigns weights 106 to the extracted features 310.

Then the module 216 combines 312 the weighted features 310 to achieve the measure of cognitive load based on the speech input of the user 200. The combination mechanism is based on a probabilistic framework that combines various classifiers 310 together. This combination mechanism can be performed as described in the co pending patent application, published as WO2006AU00914. Various models can be used to build the feature classifiers. Some of the more feasible ones include Gaussian mixture models, hidden Markov models, linear discriminate analysis, decision trees, and artificial neural networks. For example, classification scores for word-duration features can be combined with those scores for the word-category-frequency features, to improve the accuracy and robustness of the cognitive load measurement.

The result of the combination 312 is output and it represents the measure of cognitive load 218 being experienced by a user 200 for a particular task.

Depending on the proximity of this measure to an optimized pre-set cognitive load target level for that task, the next task or system output or response is verified for appropriateness or changed. For example, in the case of a distance education tutorial, if the cognitive load is too low, this feedback may be provided in real time to the tutor who can then accelerate the progress of the tutorial. If the cognitive load is too high, the interface can be automatically programmed to minimise all open applications displayed to the user (i.e. graphs on display) and to only show the video display of the tutor.

A further example will now be described where the input speech was recorded from a bush fire incident control room. The features that were identified and extracted included:

Total number of words used by the user in each level of task complexity (WordCount)
Number of words used per sentence (Words/Sentence)
Number of long words, i.e. words with at least six letters (LongWords)
Prepositions and Conjunction words, e.g. about, along, beyond, although, because, otherwise etc (AffectiveWords)
Words that denote negative emotions, e.g. annoy, angry, messy, afraid, sorry, stupid etc (NegativeEmotions)
Words that represent the human cognitive processes, i.e. think, consider, imagine, identify etc (Cognitive)
Inclusive words, e.g. and, both, each, including, plus, with etc (Inclusive)
Perception words, e.g. vision, beauty, quite, rough, cold, etc (Perception)
Words that denote feelings, e.g. hard, difficult, heavy, loose, sharp, tight, wet etc (Feelings)

Speech data sets were input into the system for various types of task. All the tasks involved different levels of difficulty or complexity to induce different levels of cognitive load. This analysis showed that the user's cognitive load while performing the different tasks was statistically different.

The table of FIG. 5 shows a summary of these results where the columns represent the features, and the rows represent the different tasks. An 'I' in a cell represents an increasing trend in the value of that feature, as calculated by the method, for the corresponding data set on the left, from low load task to the high load task. A 'D' in a cell represents a decreasing trend. Using a statistical t-test with a confidence level of 95% (alpha=0.05) and the number next to the 'I' or 'D' is the statistical p-value calculated. Every cell with a p-value of less than 0.05 represents a statistically significant result. A p-value of close to 0.05 represents a nearly significant result.

This table shows that, for all sets of speech data, the trend is stable for all selected features regardless of whether the resulting trend is significant. Additionally, for many of the features, the trend is statistically significant which confirms that these features can be used to robustly determine the user's level of cognitive load.

It will be appreciated by persons skilled in the art that numerous variations and/or modifications may be made to the invention as shown in the specific embodiments without departing from the scope of the invention as broadly described.

The cognitive load measurement method and system presented is both flexible and extensible. It is customisable and has the ability to be applied to various application areas and adapt its processing by selecting task and application specific grammatical features and perform cognitive load measurements accordingly.

Since the invention has the capability to process and analyse text transcriptions, its functionality can be easily extended to many other input modalities, not limited to just speech. For example, the user could just use the keyboard for text input, instead of the speech, to interact with the system and the system can be easily extended to record the text input and measure the user's cognitive load level normally by performing data cleaning, parsing, feature extraction, classification, and combination processes.

Similarly another example could be the use of pen input by writing the interaction text, either using a digital pen on a computer screen or using a traditional pen and a paper. The written text then can be easily converted to digital transcriptions by using some optical character recognition (OCR) technology and fed into the cognitive load module for normal cleaning, parsing, feature extraction, classification, and combination processes to evaluate load levels.

The selection of grammatical features listed above can be varied in used in any possible combination. Using Machine Learning, certain features could be weighted more heavily for particular users for particular task type, for example, if the machine learning indicates that these features provide better clues for the user's cognitive load fluctuations.

Figure 2:
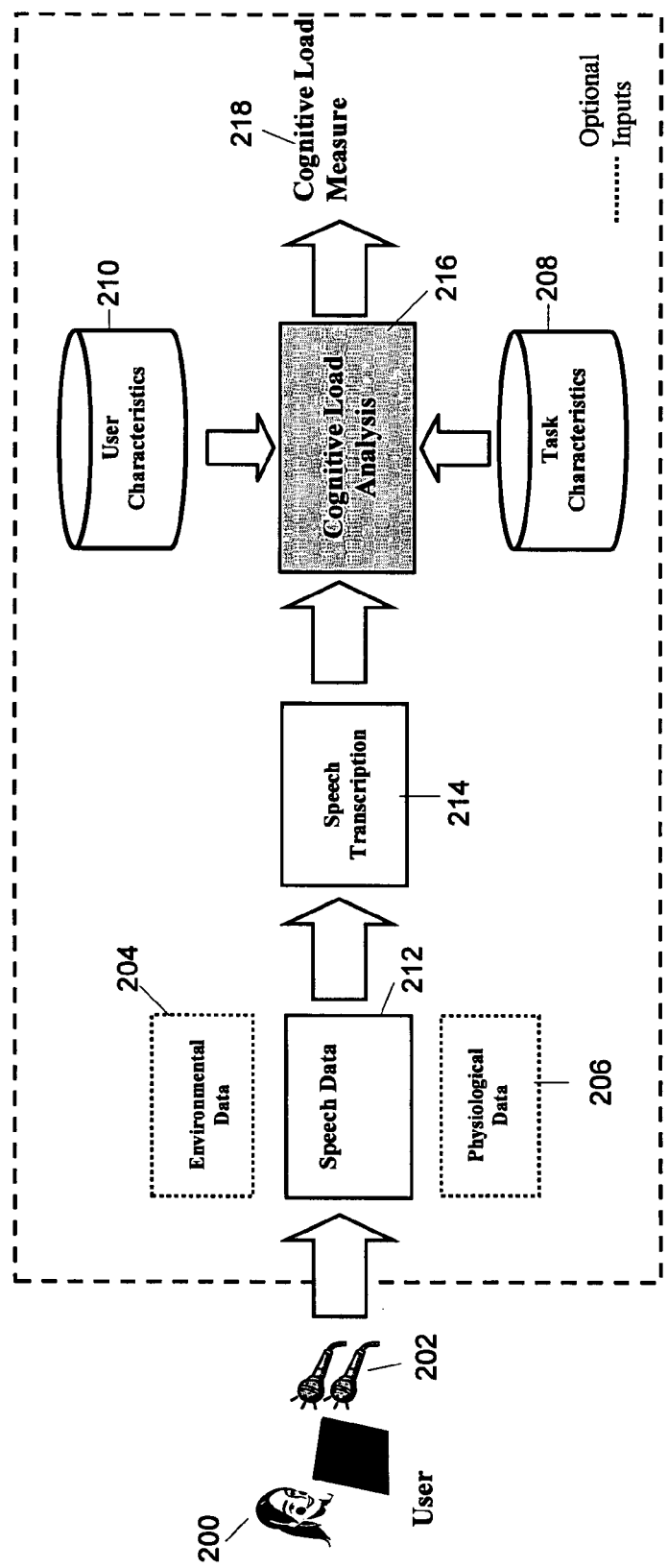
FIG. 2 is a high-level functional block diagram of the cognitive load measurement process.

As shown in FIG. 2, the cognitive load measurement can be enhanced by taking extra features other than grammatical. The user's physiological data 206 can be used which includes galvanic skin response (GSR), heart rate, perspiration. Environmental data 206 can also be used such as air temperature, or humidity and other ambient conditions.

The assessment of grammatical features could be integrated with other cognitive load measurement systems and applications. This includes multi-modal applications with cognitive load assessment capability to supplement and complement their overall performance.

The system could also be provided with any online web-based speech-enabled applications.

A text summarisation engine can be incorporated in the system to further enhance the measurement of the cognitive load of the user.

Another extension is to enable the system to perform the semantic analyses, i.e. to understand the meaning and interpretation of what the user is saying under a particular task situation. This will provide with more contextual information to improve the cognitive load measurement accuracy.

A further example of the invention is a business call centre. The users at the call centres interact with numerous customers on daily basis to satisfy their queries and provide timely support to solve their technical problems. They often work under very high pressure situations. They need to recall and retrieve relevant information in a matter of seconds and react appropriately. In such a highly stressful situation, the operators should be able to interact with the technology impeccably. The computer systems the operators use, should make the access to relevant information as easy as possible while allowing the operator to be in control of the interaction. If the system were able to customise the interface based on user's cognitive load and current situation to manage the flow of information to the operators, they would be able to handle their queries more effectively and support the customers efficiently.

The present embodiments are, therefore, to be considered in all respects as illustrative and not restrictive.

REFERENCES

[1] F. Paas, et. al., "Cognitive load measurement as a means to advance cognitive load theory". *Educational Psychologist,* 2003, 38, 63-71.

[2] WordNet, A lexical database for the English language; Cognitive Science Laboratory, Princeton University, Princeton, N.J.; http://wordnet.princeton.edu; Last accessed on 16 Sep. 2008.

[3] Language Glossary, Dept of Language and Linguistics, University of Essex, Wivenhoe Park, Colchester CO4 3SQ, United Kingdom; http://www.essex.ac.uk/linguistics/; Last accessed on 16 Sep. 2008.

[4] Wikipedia, the free encyclopedia; http://en.wikipedia.org/wiki/Grammar; Last accessed on 16 Sep. 2008.

The invention claimed is:

1. A computer-implemented method for changing an output of a user interface of a computer system based on determination of a person's cognitive load, the method comprising the steps of:
   (a) receiving, from an input device, word based input produced by a person while performing a task;
   (b) identifying automatically, using a processor, predetermined syntactical, morphological and semantic features of the word based input;
   (c) weighting and combining, using a processor, the identified syntactical, morphological and semantic features to provide a measure of the person's cognitive load;
   (d) determining the person's cognitive load, using a processor, in real-time or substantially real-time based on the measure of the person's cognitive load;
   (e) determining an output strategy of the user interface of the computer system, based on the determined cognitive load of the person; and
   (f) changing the output of the user interface of the computer system to alleviate or increase the person's cognitive load based on the determined output strategy while the person is performing the task, or after the task has been performed, wherein changing the output of the user interface of the computer system includes any one or more of:
      (i) minimizing one or more applications displayed to the person;
      (ii) showing only the displayed output for one application; or
      (iii) customizing the user interface to manage the flow of information.

2. The computer-implemented method of claim 1, further comprising the step of classifying the task.

3. The computer-implemented method of claim 2, wherein the predetermined syntactical, morphological and semantic features of step (b) are particular features relevant to that task classification.

4. The computer-implemented method of claim 1, wherein the predetermined syntactical, morphological and semantic features of step (b) include any one or more of:
   identification of the number and types of nouns, pronouns, pronouns, propositions, and verbs;
   identification of number and types of grammatical errors made;
   identification of the number and types of a particular syntax or grammatical structures;
   identification of the number and types of particular words and/or phrases at specific sentence and/or paragraph positions;
   identification of the number of shorter or longer (i.e. six letters) words and/or sentences;
   identification of semantics, meanings and interpretation of the words and/or sentences.

5. The computer-implemented method of claim 1, wherein the word based input is produced from speech of the person when performing the task.

6. The computer-implemented method of claim 2, further comprising classifying the task based on predetermined task and/or person profiles.

7. The computer-implemented method of claim 1, wherein the word based input of step (a) is text input that is typed by the person when performing the task.

8. The computer-implemented method of claim 6, wherein step (c) is based on the task and/or person profiles.

9. The computer-implemented method of claim 1 further comprising the step of receiving physiological input about the person and/or environmental data about the environment of the person while performing the task.

10. The computer-implemented method of claim 1, wherein the output strategy includes any one or more of:
    (a) modulating pace, content, and format of the output;
    (b) determining resources needed by the person to complete the task effectively and efficiently; and
    (c) verifying for appropriateness the next task or system output or response.

11. A computer system to change an output of a user interface of the computer system based on determination of a person's cognitive load while performing a task comprising:
    a receiver to receive from an input device word based input produced by a person while performing the task; and
    a classifier to identify automatically, using a processor, predetermined syntactical, morphological and semantic features of the word based input; and
    a combiner to weight and combine the identified syntactical, morphological and semantic features to provide a measure of the person's cognitive load; and
    a processor to determine the person's cognitive load in real-time or substantially real-time, based on the measure of the person's cognitive load, determine an output strategy of the user interface of the computer system, based on the determined cognitive load of the person, and change the output of the user interface of the computer system to alleviate or increase the person's cognitive load based on the determined output strategy, while the person is performing the task, or after the task has been performed, wherein changing the output of the user interface of the computer system includes any one or more of:
       (i) minimizing one or more applications displayed to the person;
       (ii) showing only the displayed output for one application; or
       (iii) customizing the user interface to manage the flow of information.

12. A computer system according to claim 11, wherein the person interacts with the computer system to perform the task.

13. Software instructions stored on a non-transitory machine-readable medium which when executed by a processor in a computer that can interface with a person, cause the processor to perform the method of changing an output of a user interface of a computer system based on determination of a person's cognitive load according to claim 1.

* * * * *